United States Patent [19]

Sipinen et al.

[11] Patent Number: 5,431,644
[45] Date of Patent: Jul. 11, 1995

[54] ELASTIC STRAND CONSTRUCTION

[75] Inventors: Alan J. Sipinen; Leigh E. Wood; Bradley W. Eaton, all of St. Paul, Minn.

[73] Assignee: Minnesota Mining and Manufacturing Company, St. Paul, Minn.

[21] Appl. No.: 40,414

[22] Filed: Mar. 31, 1993

Related U.S. Application Data

[60] Division of Ser. No. 764,982, Sep. 23, 1991, Pat. No. 5,232,777, which is a continuation of Ser. No. 464,620, Jan. 3, 1990, abandoned, which is a continuation of Ser. No. 137,258, Dec. 23, 1987, abandoned.

[51] Int. Cl.⁶ .......................... A61F 13/15; A61B 9/00; D02G 3/00
[52] U.S. Cl. .......................... 604/385.2; 2/76; 2/78.3; 2/221; 2/237; 428/167; 428/364; 428/399; 428/400
[58] Field of Search .................. 604/385.1–385.2, 604/366, 369, 378–391, 393–396; 602/75–77; 2/78 C, 221, 237, 76, 78.3; 428/107, 364, 399, 400

[56] References Cited

U.S. PATENT DOCUMENTS

| | | | |
|---|---|---|---|
| 2,708,274 | 5/1955 | Vander et al. | 2/221 |
| 2,757,381 | 8/1956 | Cottier et al. | 2/221 |
| 3,157,178 | 11/1964 | Bentov | 604/369 |
| 3,164,948 | 1/1965 | Stratford | 57/140 |
| 3,219,507 | 11/1965 | Penman | 156/244 |
| 3,572,342 | 3/1971 | Lindquist et al. | 604/373 |
| 3,575,782 | 4/1971 | Hansen | 128/156 |
| 3,632,269 | 1/1972 | Doviak et al. | 425/362 |
| 3,639,917 | 2/1972 | Althouse | 2/270 |
| 3,788,365 | 1/1974 | Campbell, Sr. et al. | 139/421 |
| 3,842,438 | 10/1974 | Campbell, Sr. et al. | 2/237 |
| 3,860,003 | 1/1975 | Buell | 128/287 |
| 3,881,381 | 5/1975 | Kalwaites | 83/170 |
| 3,916,900 | 11/1975 | Breyer et al. | 604/369 |
| 3,977,406 | 8/1976 | Roth | 604/369 |
| 4,063,559 | 12/1977 | Tritsch | 128/287 |
| 4,079,114 | 3/1978 | Bonner | 264/210 R |
| 4,081,301 | 3/1978 | Buell | 156/164 |
| 4,121,582 | 10/1978 | Masso Remiro | 602/72 |
| 4,237,889 | 12/1980 | Gobran | 128/287 |
| 4,253,461 | 3/1981 | Strickland et al. | 128/287 |
| 4,300,562 | 11/1981 | Pieniak | 128/287 |
| 4,324,245 | 4/1982 | Mesek et al. | 128/287 |
| 4,337,771 | 7/1982 | Pieniak et al. | 128/287 |
| 4,352,355 | 10/1982 | Mesek et al. | 128/287 |
| 4,381,781 | 5/1983 | Sciaraffa et al. | 604/372 |
| 4,397,645 | 8/1983 | Buell | 604/385.2 |
| 4,437,860 | 3/1984 | Sigi et al. | 604/385 |
| 4,525,407 | 6/1985 | Ness | 428/138 |
| 4,552,795 | 11/1985 | Hansen et al. | 428/110 |
| 4,563,185 | 1/1986 | Reiter | 604/385 |
| 4,610,681 | 9/1986 | Strohbeen et al. | 604/396 |
| 4,626,305 | 12/1986 | Suzuki et al. | 156/164 |
| 4,628,655 | 12/1986 | Scheiderer | 52/397 |
| 4,640,859 | 2/1987 | Hansen et al. | 428/105 |
| 4,642,819 | 2/1987 | Ales et al. | 2/400 |
| 4,643,729 | 2/1987 | Laplanche | 604/389 |
| 4,769,283 | 9/1988 | Sipinen et al. | 428/343 |
| 5,232,777 | 8/1993 | Sipinen et al. | 604/389 |

FOREIGN PATENT DOCUMENTS

| | | | |
|---|---|---|---|
| 095034 | 11/1983 | European Pat. Off. | A41B 13/02 |
| 674134 | 1/1930 | France . | |
| 1563155 | 4/1969 | France | B29D 7/00 |
| 3423644 | 6/1984 | Germany | A41B 13/02 |
| 952419 | 3/1964 | United Kingdom . | |
| 2118021 | 10/1983 | United Kingdom | A41B 13/02 |

OTHER PUBLICATIONS

"There's a Fortune to be Found in a Waistland".

Primary Examiner—Randall L. Green
Assistant Examiner—K. M. Reichle
Attorney, Agent, or Firm—Gary L. Griswold; Walter N. Kirn; William J. Bond

[57] ABSTRACT

An elastic strand construction comprising a plurality of spaced ribs separated by thin zones is provided. The elastic strand construction is preferred for applications in disposable garments or the like. A method of manufacturing the preferred elastic strand comprises extrusion of polymeric material through a profiled die or the like. In the alternative, a method of formation comprising extrusion between a profiled roller arrangement is described. A preferred disposable garment construction utilizing elastic strands according to the present invention is described.

4 Claims, 3 Drawing Sheets

ELASTIC STRAND CONSTRUCTION

This application is a divisional of application Ser. No. 07/764,982, filed Sep. 23, 1991, now U.S. Pat. No. 5,232,777; which is a continuation of application Ser. No. 07/464,620, filed Jan. 3, 1990, now abandoned; which is a continuation of application Ser. No. 07/137,258, filed Dec. 23, 1987, now abandoned.

FIELD OF THE INVENTION

The present invention relates to the construction of elastic members utilizable in disposable diapers or similar articles. More particularly, the present invention relates to elongate elastic members formable from extrusion processes or the like, and having preferred, advantageous, physical characteristics.

BACKGROUND OF THE INVENTION

Elastic or stretchable strands have found considerable use, especially in the disposable garment industry. The term "disposable garment" is meant to refer to articles intended to be worn only once or temporarily, with ultimate disposal rather than laundering. Examples include: diapers; adult incontinence garments; hospital garments such as surgical gowns, caps or shoe covers; disposable pajamas; laboratory coats; shower caps and similar items. Generally, such garments are made of lightweight film or sheet material such as: thermoplastic materials; non-woven coated films or papers; or, composites of one or more of these types of materials. Since low cost manufacture is generally a critical requirement, such garments are often manufactured using techniques such as die-cutting, adhesive-bonding, heat-sealing and sonic-sealing; rather than through application of stitching or sewing methods utilized in more expensive, longer-lasting, textile garments.

It has been found desirable in such garments to provide elastic constructions in the vicinity of openings, such as to accommodate a wearer's arm, neck, waist, head or leg. Elasticity in these portions of the garment accomplishes numerous functions including: insuring snug fit for a variety of sizes of users; and, in instances such as disposable baby diapers, providing for a sealing or containing construction, for example around a baby's legs, to prevent or reduce leakage.

Two primary, related, forms of providing for elasticized openings have been developed. In a first of these an elastic member is stretched and is attached to the article in an elastically contractible condition. After attachment to the article, tension is released and the elastic strand contracts, bunching up or shirring the article. A strand, for example, so attached around a leg opening will cause the leg opening to contract. If the contracted leg opening is smaller in diameter than a leg projecting therethrough during use, in such use the elastic member will be stretched open somewhat, and will press snugly against the leg member, generating a snug fit or closing relationship.

A variety of methods of attachment of the elastic member to the garment or substrate have been developed. These include heat-sealing, sonic welding and pressure-sensitive adhesives or the like. In some instances spaced adhesive units have been utilized to advantage, in providing for relative strength or preferred shirring patterns.

A variety of elastic strand constructions, for utilization as described above, have been developed. Included in these are single strand arrangements. A problem with such arrangements is that they are relatively susceptible to problems with failure, unless made relatively strong. A reason for this is that the failure of a single point of attachment or adhesion can cause a complete product failure. Further, should the single elastic member fracture or break, substantially complete failure may also result.

Another problem with a single strand arrangement is that only a relatively narrow seal or closure is formed; and, if made relatively tight, irritation to the wearer's skin in a very narrow, localized, region or band may result.

As a result of the above problems, a variety of alternates to a single narrow band arrangement have been developed. For example, a plurality of individual, spaced, bands have been utilized to provide a rather wide elastic area. Also, net arrangements, i.e. cross-connected bands, have been developed. In some instances relatively wide elastic tape arrangements have been proposed. Also, a wide band comprising a plurality of elongate members fused, longitudinally, to one another has also been developed.

While the above-described arrangements have their uses and advantages, none is completely satisfactory. In multiple strand arrangements or net arrangements, attachment to the substrate or garment may pose a problem. A reason for this is that only a relatively narrow point for adhesive attachment is provided, i.e., a point of engagement between a relatively narrow strand member and the wider substrate. A narrow point of adhesion poses a substantial risk of failure, and thus is a problem. Further, multiple strand arrangements can be relatively expensive to construct, as complicated and precise attachment mechanisms and adhesive application arrangements may be required.

Net arrangements may have advantages but can still pose problems, due in part to cost of formation. Also, if thin or narrow strips are used, attachment may still be difficult.

Wide, thick, elastic strips are also not completely satisfactory. In some instances, they may be so thick and strong not to stretch sufficiently for comfort. In other instances, they may be relatively expensive to produce, since a relatively large amount of material may be used in their construction.

A second major method of providing for an elastic strand member on a substrate such as a disposable garment or the like, is through utilization of a strand of heat shrinkable elastic material. Generally, the material is affixed to the substrate in a dimensionally heat unstable state. The substrate and elastic member combination is then exposed to activating heat, to shrink the elastic component and generate gathering or shirring. If properly chosen, the material used for the elastic strand can be provided such that once shrunk it will be appropriately elastic, and thus will stretch around an arm, leg, neck, etc. to provide the desired closing or sealing relationship.

The heat-shrunk approach has been utilized in a variety of physical embodiments. For example, multiple strand arrangements may be utilized, as well as net arrangements and the like. In at least one application, multiple strands have been provided within a composite substrate arrangement.

The problems with conventional heat shrinkable elastic strand arrangements have generally been parallel to those described above. If multiple strand arrangements are utilized, they may be relatively complicated to construct or apply. Composite structural relationships may be too expensive for use in many types of disposable items. Problems with placement of adhesive may result, if relatively narrow strands are used. If relatively wide strands are used, there may be problems with insufficient elasticity and/or excessive cost of materials.

It is important to note again that a primary use of elastic strands such as those of concern is to provide for shirring of substrates in disposable garments. It is significant, therefore, to maintain costs at or near a substantial minimum in order to obtain a competitive advantage. Thus, relatively complicated composite arrangements, relatively complicated multi-strand attachment mechanism and relatively difficult to utilize adhesive arrangements are generally to be avoided, if possible. Further, it is preferred to utilize a minimum amount of elastic strand material per substrate or garment, in order to maintain low construction costs. It is important to provide an elastic construction which will be efficient and effective, in order to accommodate the demands of the marketplace and competition.

What has been needed has been an elastic strand construction which is relatively easy to achieve and to mount on or in association with substrates such as disposable garments or the like. Further, what has been needed has been such a strand construction which is efficient and effective in use, to provide for a good, comfortable closing or sealing arrangement when utilized around an arm or leg aperture, or the like. Finally, there has been a need for such an elastic strand which can be manufactured in large quantities relatively quickly, efficiently, and inexpensively.

SUMMARY OF THE INVENTION

The present invention concerns: a preferred elastic strand construction; a method of forming elastic strands of the preferred construction; preferred methods of use of elastic strands constructed according to the present invention; and, disposable garment constructions utilizing elastic strands of the preferred construction.

Elastic strands arrangements according to the present invention comprise: an elastic strand having a plurality of laterally spaced longitudinal ribs, each of which has at least a first thickness.

A preferred method of manufacturing an elastic strand according to the invention includes the steps of: providing a die having an orifice shaped to define a plurality of thick zones, each of which is separated by a thin zone, in material extruded therethrough; providing a hot extrudable thermoplastic elastomer; extruding the hot thermoplastic elastomer through the profiled die to form a hot ribbon of extruded elastomer having: a plurality of laterally spaced longitudinal ribs, each of which has at least a first thickness; and, a substantially continuous longitudinal transition zone extending between and attached to each of the longitudinal ribs, each transition zone having a thickness less than the first thickness and substantially equal to the profiled die thin zone; and, quenching the hot ribbon.

An alternate method of manufacturing an elastic strand according to the present invention includes the steps of: providing a hot extrudable thermoplastic elastomer; providing an extrusion system for generating a hot elongate ribbon of the thermoplastic elastomer; providing a roller system including first and second rollers having a nip therebetween; the first roller having a profiled outer surface including a plurality of spaced substantially parallel grooves therein; extruding the elastomer through the extrusion system to form a hot elongate ribbon; directing the hot elongate ribbon through the nip in the roller system, wherein the first roller outer surface forms a plurality of elongate parallel longitudinal ribs in the ribbon; and cooling the ribbon after formation of the ribs therein.

A proposed method of manufacturing thermally unstable, heat shrinkable strands according to the present invention includes the step of length orienting the strands subsequent to formation by one of the methods described above. Length orientation involves stretching the strand at somewhat elevated temperatures and allowing the strand to cool while held in the stretched state. Process conditions, i.e. temperature, nip pressure, length differential, will be dictated by the desired amount of stretch and the chemical composition of the strands, and are easily selected by those skilled in the art.

A preferred article, such as a disposable diaper, according to the present invention comprises: a substrate; and, an elastic strand mounted on the substrate, the elastic strand having: a plurality of laterally spaced ribs, each of the ribs having at least a first thickness; and, a substantially continuous longitudinal transition zone extending between and attached to each longitudinal rib, each transition zone having a thickness less than the first thickness.

In general, elastic strands according to the invention comprise longitudinally contoured or ribbed unitary strips. That is, each strand has spaced thicker zones or ribs preferably running lengthwise, and substantially no apertures or net construction. Substantially continuous transition or thinner zones run substantially completely along and between the elongate thicker zones or ribs, spacing each rib from the next adjacent rib. The thicker ribs, as a result of the separation, in part constitute individual regions of contraction force. The thinner zone(s) constitute a means of combining the partially independent thicker elastic zones or ribs into a unitary construction, for ease of manufacture, application and use. While all embodiments of the present invention include a plurality of spaced ribs, it is noted that at least one embodiment (that of only 2 ribs) may include only one thinner or transition zone.

Certain preferred elastic strands according to the present invention have one substantially flat, i.e. non-ribbed, side to facilitate mounting to the substrate. That is, for this embodiment the strand has opposite surfaces, one of which is flat, the other having the ribs thereon and projecting outwardly therefrom. The relatively flat side facilitates mounting since it provides an overall relatively broad surface for engagement with adhesives or for heat-sealing, sonic-welding, etc. As a result, failure of adhesion at any particular local point is not likely to substantially inhibit overall operability of the elastic strand in providing the shirred construction. Further, attachment to a substrate is relatively simple, since only one relatively wide strand is used, with problems of handling multiple, narrow, strands avoided.

Preferred elastic strands according to the present invention are made from extrudable thermoplastic elastomeric materials. According to one preferred method of manufacture, the desired strand construction is formed by extruding of hot thermoplastic material through an appropriately profiled die. Such an extrusion process is generally followed by immediate quenching, in a water bath or the like, to facilitate retention of the desired physical shape.

According to an alternate method of forming elastic strands profiled according to the present invention, an elongate extruded strip of relatively hot moldable thermoplastic material is directed through a nip between adjacent rollers of a roller mechanism. At least one of the rollers is provided with a profiled surface of appropriate desired form. Preferably, at least one of the rollers is a chilled roller or cold roller, facilitating cooling of the elastic strand sufficiently so that the molded strand will retain its shape.

Preferred methods of use of elastic strands according to the present invention involve attachment to a substrate to be shirred, by means of adhesives, sonic-welding, heat-sealing or similar techniques. If non-heat shrinkable elastomeric strands are formed, generally the method of use involves stretching the elastic strand material a desired amount, before attaching it to the substrate. For this method, attachment occurs while the elastic strand is under tension, so that once attached and when tension is released, a bunching, gathering or shirring of the substrate occurs. If heat shrinkable strands are formed, as described supra, they may be attached without substantial tension, and then heat-treated to shrink and cause shirring.

The present invention also concerns an overall substrate or garment arrangement having an elastomeric portion formed from attachment of an elastic strand as described above, to a selected portion of the substrate.

The drawings constitute a part of this specification and include exemplary embodiments of the present invention while illustrating features thereof. It will be understood that in some instances relative material thicknesses, and relative component sizes, may be shown exaggerated for clarity. It will also be understood that some of the drawings are schematic only and thus are representative of a variety of methods or constructions that may be utilized.

DETAILED DESCRIPTION OF THE PREFERRED AND ALTERNATE EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed system or structure.

The Elastic Strand Construction

Figure 1:
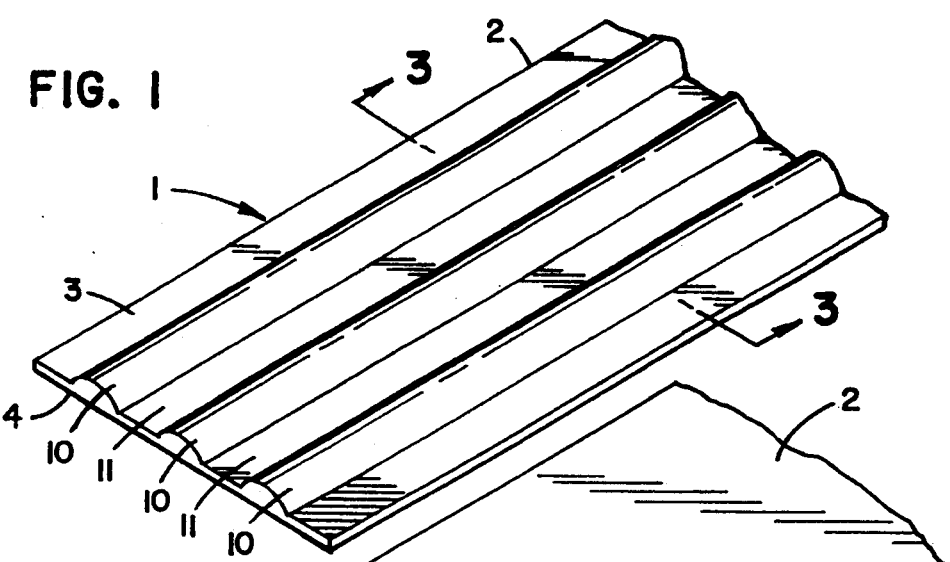
FIG. 1 is a fragmentary top perspective view of an elastic strand arrangement according to the present invention.
Figure 2:
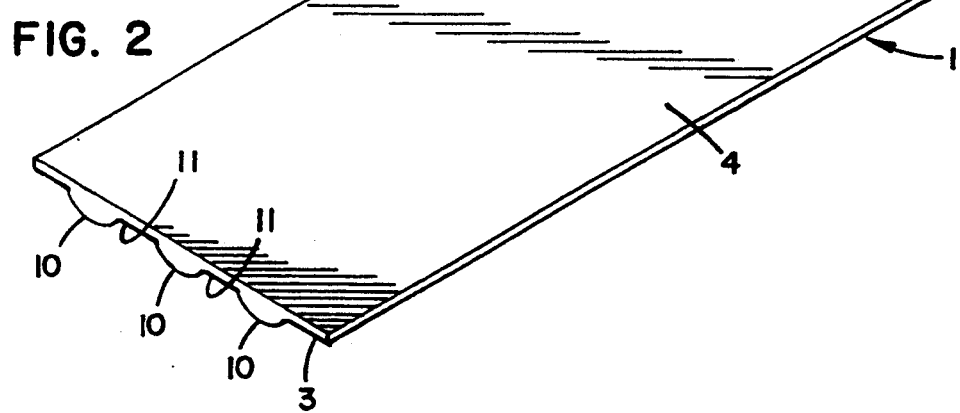
FIG. 2 is a fragmentary bottom perspective view of the arrangement shown in FIG. 1.
Figure 3:
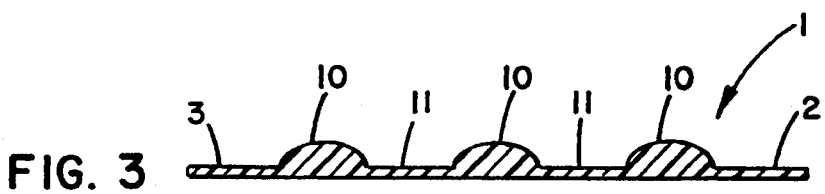
FIG. 3 is a cross-sectional view taken generally along line 3—3, FIG. 1.

FIGS. 1–3 illustrate a preferred elastic strand arrangement according to the present invention. Referring to FIG. 1, the reference numeral 1 generally designates the preferred strand construction. Strand 1 comprises an elongate strip 2 having first and second opposite surfaces or surface portions 3 and 4 respectively. Strip 2 is continuous and unitary in construction; that is, it is formed in one piece and preferably does not contain any pattern of apertures or holes therein. As a result of this construction, attachment of strip 2 to a substrate, such as a disposable garment or diaper, is facilitated. A reason for this is that relatively large areas of strand are available as bonding sites. For the embodiment shown in FIGS. 1–3, surface 4 provides a bonding surface for attachment to a garment or the like. For the preferred embodiment depicted, surface 4 is substantially flat, FIG. 2, thus facilitating the attachment process.

Unitary strip 2 includes thereon a plurality of spaced ribs, or thick zones, 10. The ribs 10 preferably extend substantially parallel to one another along the entire length of strip 2. The ribs 10 are spaced from one another by substantially continuous thin zones or areas 11. Preferably strip 2 is formed from an elastomeric substance in such a way, for example as described below, that the composition of strip 2 is constant throughout. That is, the thin zones or areas 11, and the thick zones or ribs 10, are formed of the same material. For the preferred embodiment, ribs 10 are formed in, and protrude outwardly from, surface 3.

The purposes of the thick zones 10 and thin zones 11 differ somewhat, and advantages are obtained from the presence of both. The thick zones 10 provide, to a great extent, for much of the longitudinal strength and elasticity of strip 2. That is, the ribs 10, being thick and of an elastomeric substance, provide for significant retractive tensile force.

The relatively thin zones 11 provide unique advantages. First, they facilitate attachment of multiple ribs 10 to the substrate, since the zones 11 maintain the ribs 10 in proper position with respect to one another and permit all ribs 10 to be readily handled by a single applicator or application device, simultaneously. Further, in the preferred embodiment, the thin zones 11 provide a broad surface for attachment of adhesives or the like, to facilitate attachment to almost any substrate.

An overall spaced relationship between the ribs 10, maintained by thin zones 11, is preferred for numerous reasons. First, a relatively broad elastic band width is provided. A broad elastic band both is aesthetically pleasing and more comfortable. Also, a better seal or enclosure results, since a greater surface area is involved. Failure of a single rib 10 is unlikely to substantially detract from elasticity of the overall arrangement since other ribs are present and the thin zones 11 will help disperse tension. Further, any crimp which may form in a portion of strip 2, or any sharp object brought in association therewith, will be unlikely to substantially adversely affect all ribs 10 at the same time. Thus, the structural integrity of strip 2 is more easily maintained during application, use and under stress conditions.

For the embodiments shown in FIGS. 1–3, the strip 2 is depicted with three ribs 10. It will be understood, however, that a plurality of alternate embodiments may be provided, having various numbers of longitudinal ribs 10, and thin zones 11. Included in the possibilities is an embodiment, not shown, including two ribs separated by a single thin zone.

In FIG. 3 a cross-section of strip 2 is depicted. From FIG. 3, it will be understood that the zones 11 are very thin, relative to the ribs 10. While a variety of ratios of rib thickness to thin zone thickness may be utilized in arrangements according to the present invention, generally ratios between about 2/1 and about 10/1 will be preferred. Such ratios lead to acceptable overall integrity, while at the same time retaining much of the longitudinal strength, and elasticity of the overall arrangement, in the rib portions of the strip 2.

It will be understood that the overall thickness of the strip 2, and particularly the ribs 10 thereof, will depend in part upon the nature of the elastomeric material from which the strip 2 is formed, and also the overall strength of strip 2 is intended. For preferred applications, such as strips for disposable diapers or the like, the overall thickness of the ribs 10 will generally be in the range of 0.100 millimeters (mm) to 0.635 mm, and preferably about 0.150 mm to 0.635 mm.

The overall width of the thick zones, and thin zones, is generally dictated by the overall strength of the strip desired, and the width of elastic band desired for a particular application. For most applications involving unitary strips 2 for attachment to disposable diapers or the like, the range of widths for the thicker zones will generally be about 0.250 mm to 5.1 mm, and preferably about 0.760 mm to 2.5 mm, and the overall width of the thinner zones 11 will be in the range of about 0.250 mm to 5.10 mm, preferably 0.760 mm to 2.50 mm.

Preferably the thin zones 11 are relatively wide, by comparison to the width of the ribs 10, to insure that the ribs 10 are well spaced apart. One reason for this is that in many applications it is desired to insure that the ribs 10 can, at least in part, act independently of one another as stretching elements. Thus, again, failure of one is unlikely to affect the others. Another reason for broad spacing is to avid injury to adjacent ribs, if one rib is brought under stress from crimping or contact with a sharp object or the like. Another reason for relatively wide spacing is to generate a relatively wide elastic band, to reduce skin irritation. Preferably, the width of the average thinner zone 11 is at least 50 percent of the width of the average rib 10. It will be understood that the thin zones 11 need not all have the same width.

From FIG. 2, an advantage to the preferred embodiment having the relatively flat lower surface 4 is apparent. Since surface 4 is relatively broad, and flat, adhesive can be readily applied between surface 4 of strip 2 and a portion of a substrate such as a disposable diaper or the like.

It is noted that the ribs 10 of the embodiment of FIGS. 1–3 have a generally rounded outer surface, corresponding to a semi-oval, or semi-circular arrangement, It will be understood that a variety of shapes may be utilized. For example, in FIG. 4, a cross-section of an embodiment is illustrated wherein the ribs 20 have a generally square cross-section and are separated by transition zones 21. In FIG. 5, an overall oval cross-section for ribs 22 is shown. From comparison of FIGS. 3, 4 and 5 it will be understood that a variety of cross-sectional shapes can be provided. Each of the types of cross-sections shown may have advantages for particular applications, especially relating to general overall aesthetics, strength, stretch and ease of manufacture.

Figure 4:
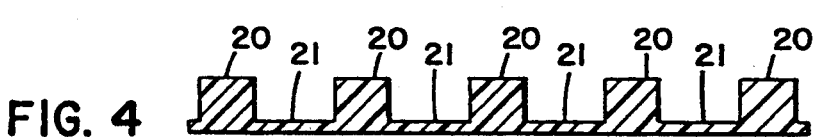
FIG. 4 is a cross-sectional view of an alternate embodiment of the present invention.
Figure 5:
FIG. 5 is a cross-sectional view of a second alternate embodiment of the present invention.

It is noted that each of the embodiments of FIGS. 3, 4 and 5 has a surface, corresponding to lower surface 4, FIG. 3, which is relatively broad and flat. While advantages can be obtained from such an arrangement, such a flat surface is not required to obtain some of the advantages of the present invention, as is illustrated by the embodiment of FIG. 6.

Figure 6:
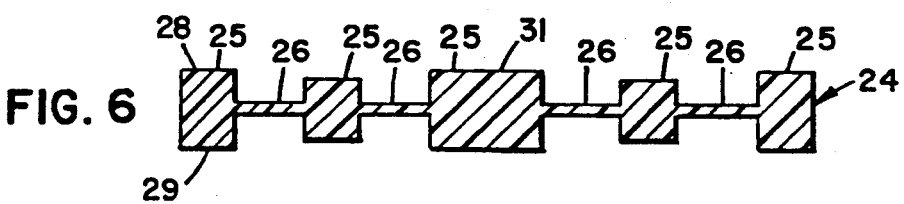
FIG. 6 is a cross-sectional view of a third alternate embodiment according to the present invention.

In FIG. 6, an overall unitary strip 24 having a plurality of ribs 25 attached to one another by means of elongate thin zones 26 is shown. The embodiment of FIG. 6 differs significantly from that of the previous figures, in that the ribs 25 project in both directions (here shown as up and down) from thin zones 26; that is, opposite surfaces 28 and 29 both have ribs therein. Such an arrangement may be preferred, in some situations, for aesthetics. Also, such an arrangement may lead to a more consistent stretch of each rib 26, along its cross-section, during stress, for example during application to a substrate. That is, upper and lower surfaces 28 and 29 may be stressed substantially the same during stretching and application. Such would not as readily be the case, for example, for the embodiment in FIG. 5 since lower portions of the ribs 20 are in a different spatial relationship with respect to the transition zones 21, than are upper portions of the ribs 20.

It is noted that the embodiment of FIG. 6 may, in some applications, be somewhat more difficult to mount than the previously described embodiment, since no extremely broad flat surface is provided to facilitate mounting. Nevertheless, especially if a strip according to FIG. 6 were manufactured of sufficiently soft material, it could be squeezed flat enough to facilitate mounting. Further, if at least some ribs having a sufficiently wide cross-section are chosen, mounting will be facilitated. This is exemplified in FIG. 6, by the particularly wide central rib 31. It will be understood that although for the embodiment shown in FIG. 6 the opposite surfaces 28 and 29 are substantially identical, there is no requirement that they be so. That is, the ribs of different surfaces may have different profiles, and indeed may not necessarily be located opposite one another.

For the embodiments shown in FIGS. 3 and 4, all ribs had a substantially identical cross-section. It will be understood by comparison of FIGS. 5 and 6, that such is not required in all embodiments. Ribs having different areas of cross-section, and indeed different overall shapes, may be utilized to advantage in a number of ways. For example, different rib thicknesses, i.e., sizes and strengths, may provide for increased strength and resistance to stretching over one selected portion of the overall strip width. This may be useful, for example, in providing a snug fit in a portion of a garment or the like sized for fitting over a member not of constant cross-sectional area. For example, a typical person's wrist grows larger in circumference as the elbow is approached. If a wide elastic member according to the present invention is to be utilized in a cuff of a garment, it may be desired to have a portion closer to the elbow be less resistant to stretch, than a portion close to the hand, in order to facilitate comfort. This could be readily accomplished through the utilization of ribs which are relatively thin, nearer the elbow, by comparison to those ribs nearer to the hand.

Another reason why a variety of shapes or designs of ribs may be desired, is for aesthetics. While items according to the present invention are generally intended to be disposable, attractive designs may often still be desired, and may be achievable in strips according to the present invention.

Method of Formation

A particular advantage to elastic strand constructions according to the present invention is that they may be rapidly, efficiently, conveniently and relatively inexpensively manufactured. A reason for this is that the overall unitary construction lends itself toward manufacture from extrusion techniques. Since no netting, or aperture, arrangement is involved, the manufacturing process is facilitated. Two particularly convenient methods of manufacture are depicted in FIGS. 7-11. The method of FIGS. 7 and 8 concerns formation by extrusion through a profiled die. The method of FIGS. 9-11 concerns formation by extrusion through a nip between rollers.

A. Formation by Extrusion through a Profile Die

Generally, the material from which unitary strands according to the present invention are formed is such that when it is hot it is substantially pliable and/or formable, but once cooled it retains a selected configuration. As previously explained, the unitary strands according to the invention may be of either of two types, a first type which is formed into a construction for application to a substrate in a stretched state; and a second type which is formed thermally unstable, so that when heated it will shrink considerably to shirr a substrate to which it is attached. Either of these forms may be manufactured by either of the methods described herein.

Figure 7:
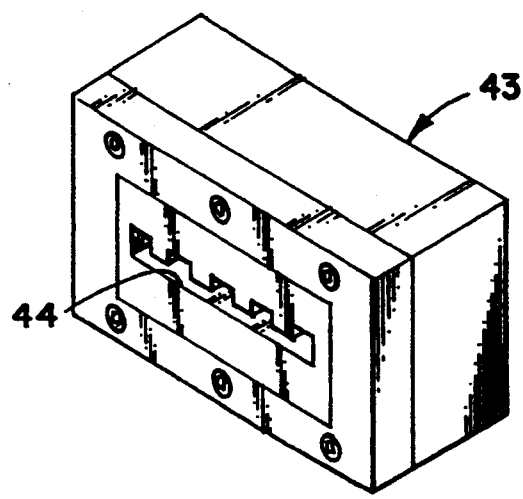
FIG. 7 is a fragmentary perspective view of a profile die arrangement utilizable for creation of an elastic strand according to FIG. 1.

Since the raw material for formation of the unitary strands according to the present invention is extrudable when hot, a particularly efficient method of manufacture involves extrusion through a profile die, i.e. a die of appropriate configuration for shaping hot material extruded therethrough. Referring to FIG. 7, die 43 is depicted having a profiled channel 44 of appropriate shape to form a unitary strand according to the present invention. It will be understood that profiled channel 44 may have a variety of shapes, to accommodate unitary strands of different configurations. The channel 44 of die 43 depicted is of a shape appropriate to form the strand of FIG. 4. Die 43 is shown as being such that channel 44 may be removed and replaced by a channel of different shape, if desired.

Generally strands of the present invention are produced by: extruding the hot polymer or polymer blend, typically at a temperature of about 150° to 235° C., through a profiled extrusion die such as die 43; and, quenching, typically upon passing the formed strand through a water-filled quench tank with a submerged take-away. This process is represented, schematically, in FIG. 8.

Figure 8:
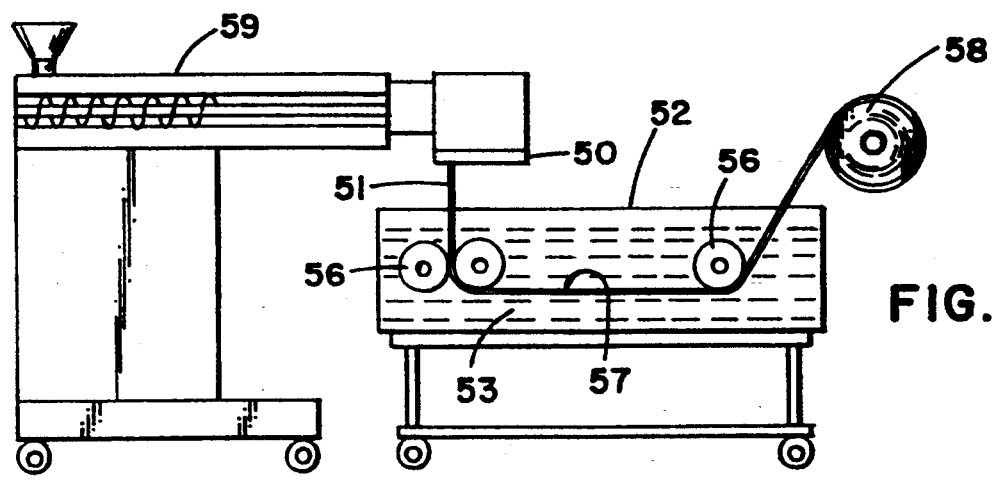
FIG. 8 is a schematic elevational view of a method of forming an elastic strand arrangement according to the present invention.

Referring to FIG. 8, profiled die 50 is depicted with a line or ribbon 51 of hot extruded material extending therefrom, into quench tank 52. Tank 52 is filled with water 53, which water may be cooled in some instances, to for example 4°-16° C. Upon quenching the ribbon 51 is cooled sufficiently to retain its shape. Idler rollers 56 are shown directing the quenched ribbon 57 to a storage roller 58.

The example represented in FIG. 8 utilizes a profiled die that has the approximate shape of the final strands. In preferred applications the ratio of the land length to the opening height of the profiled die is at least 10. This ratio is the length of the flow path through the die, to the thickness of the opening. While other ratios may be utilized, in preferred applications, such a ratio will be used as it leads to ready formation of desired strands. In FIG. 8, reservoir and extruder 59 is shown forcing material through die 50.

Desired extruded shapes can be made from profile dies cut other than with the desired final shape; for example by varying land length to change the flow pattern through the die plate in order to cause more (or less) material to flow through specific regions. Such dies are less flexible with respect to varying materials and run conditions, and therefore are not preferred.

B. Shaping through Utilization of a Profiled Roller Arrangement

Figure 9:
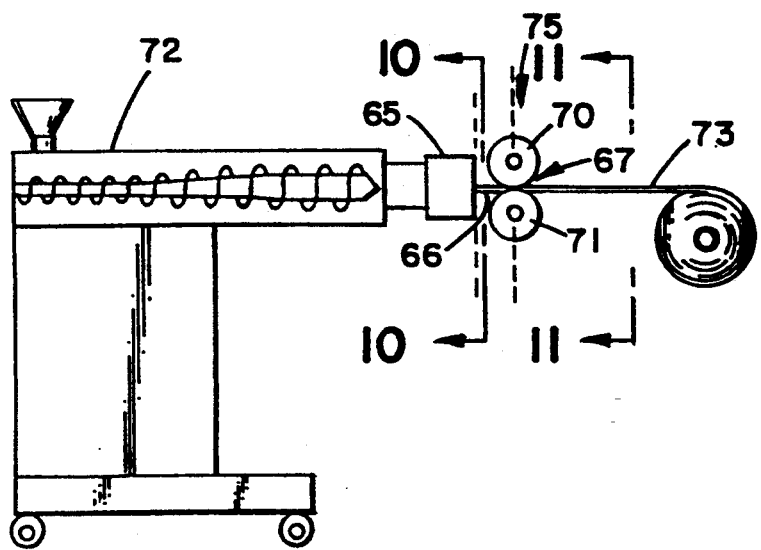
FIG. 9 is a elevational schematic view of an alternate method of forming an elastic strand arrangement according to the present invention.
Figure 10:
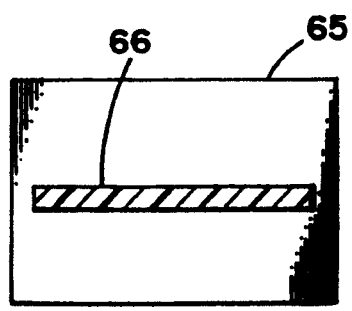
FIG. 10 is a cross-sectional view taken generally along line 10—10, FIG. 9.
Figure 11:
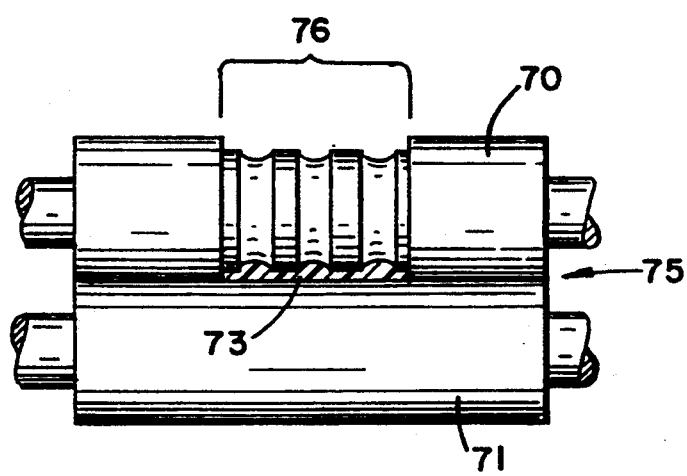
FIG. 11 is a fragmentary cross-sectional view taken generally along line 11—11, FIG. 9.

FIGS. 9-11 depict an alternate method of construction of unitary strands according to the present invention. Generally, the method involves extrusion between rollers appropriately profiled to cause a preferred confirmation in the strand. The overall method is depicted schematically in FIG. 9.

Referring to FIG. 9, an extruder in combination with a slot extrusion die 65 is shown with a ribbon 66 of hot moldable extrudate projecting outwardly therefrom. The ribbon 66 is passed through a nip 67 between rollers 70 and 71. Reference numeral 72 designates a reservoir and extruder of polymer material.

Preferably at least one of the rollers 70 and 71 is chilled, that is it is cooled sufficiently so that it will cause product ribbon 73 to retain the desired profile or configuration.

Rollers 70 and 71 form an overall roller mechanism 75 profiled in a manner causing a preferred shaping of hot ribbon 66 as it passes therethrough. For example, roller 70 may include slots, grooves or the like therein, which generate a preferred shape of ribbon 73. Referring to FIGS. 10 and 11, an example is given. In FIG. 10 a side elevational view of ribbon 66 is presented. It will be understood that die 65 provides ribbon 66 with a generally rectangular, i.e. non-profiled, cross-section.

In FIG. 11, formed ribbon 73 is shown passing outwardly from between rollers 70 and 71. The rollers 70 and 71 are profiled appropriately to give ribbon 73 a selected shape. In particular, roller 70 is shown profiled at section 76, by means of recessed parallel grooves, to give ribbon 73 a cross-sectional shape analogous to strand 2, FIG. 1. It will be understood that a variety of selected shapes may be similarly formed. Preferably, the method is utilized to provide strands having the desired elongate longitudinal ribs separated by thin zones.

Preferred chilling temperatures for the chilled roller(s) will primarily depend upon the elastomer composition, melt viscosity and contact time.

Use of the Elastic Strands in Articles

Figure 12:
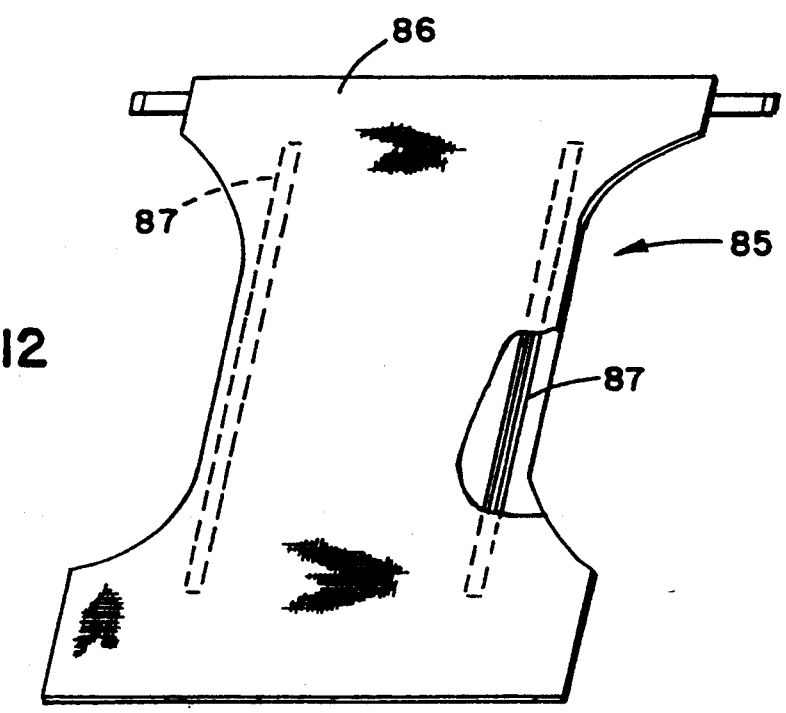
FIG. 12 is a perspective view of a disposable diaper incorporating an elastic strand arrangement according to the present invention, with portions broken away to show internal detail.

It will be readily understood that the unitary elastic strands of the invention may be utilized in a variety of articles and in a variety of manners. It is anticipated that a preferred use will involve applications to disposable diapers, incontinence garments or the like, particularly around leg apertures. Such an application is illustrated in FIG. 12. Referring to FIG. 12, a disposable diaper arrangement 85 is depicted. It will be understood that the arrangement 85 may be of a variety of designs shapes or configurations. Generally, diaper 85 comprises a substrate 86, to be provided with elastic bands. Specifically, attached to the substrate 86 are strips 87 or unitary strand material according to the present invention. The strips 87 may be mounted, if desired, between layers of an overall composite construction for substrate 86. For the embodiment shown in FIG. 12, strips 87 are represented by phantom lines, to indicate that indeed they are out of view, underneath protective layers.

Application of straps 87 to substrate 86 may be accomplished by a variety of means, including efficient mechanical means involving application of the strips 87 from a feed roller with utilization of various cutting and adhesive mechanisms; or, through utilization of various sonic-welding or heat sealing methods. As has previously been explained, in some instances strip 87 may be formed such that it is applied in a thermally stable, but stretched state, with shirring automatically caused once the tension is released. In the alternative, strips 87 may be thermally unstable, heat-shrinkable material as described supra, applied in an untensioned state, and then treated with heat to shrink and cause appropriate shirring.

Elastic Strand Composition

Materials useful in making unitary strands of the present invention include a wide variety of thermoplastic elastomers. An elastomer is a substance which, in a stable from when stretched and released, will retract to resume its original dimensions or nearly so. Some preferred elastomers are defined by ASTM Special Technical Bulletin No. 184, requiring that after the elastomer: is stretched at room temperature to twice its original length; is held for a five minute period; and, is released; it returns to within 10 percent of its original length within five minutes. Furthermore, it is a requirement of preferred elastomers for use according to the present invention that they readily soften or melt to an extrudable viscosity.

Suitable thermoplastic elastomers include elastomeric ethylene-propylene rubbers and random or block polymers of ethylene and two other monomers such as propylene or a diene, for example, 1,4-hexadiene. Preferably, the ethylene content is from about 50 to 70 weight percent, and more preferably 55 to 65 percent by weight. Also, preferably, the propylene content is from 25 to 50 percent by weight, more preferably 35 to 45 percent by weight. Preferred diene content is from about 0.5 to 4.0 weight percent, more preferably 1 to 3 weight percent. For preferred elastomers according to the present invention preferred dienes include: dicyclopentadiene; 1,4-hexadiene; methylene norbornene,; ethylidene norbornene; cyclooctadiene; or structurally similar compounds.

Other suitable elastomeric polymers can be selected from several chemical classes including: block copolymers of aromatic-aliphatic polymers, particularly the linear ABA, radial A—$(BA)_n$ and multiblock ABABA polymers such as styrene-isoprene-styrene, styrene-butadiene-styrene, styrene-butylene-ethylene-styrene and the like, ethylene-vinyl acetate copolymers with high vinyl acetate content (for example Elvax 260 which has a sufficient vinyl acetate content (28%) to exhibit elastomeric properties), and thermoplastic polyurethanes and extrudable copolyester-ethers. Specific properties and sources of flexible polymers of these three classes are disclosed in Kirk-Othmer, *Encyclopedia of Chemical Technology*, Vol. 8, pp. 626–640 (3rd ed. John Riley & Son, New York, N.Y.), incorporated herein by reference.

Combinations, mixtures and blends of the thermoplastic elastomers can also be used as alternatives to the pure elastomers.

Preferred thermoplastic elastomers are those generally referred to as ABA block copolymers. Examples of these were listed above and include styrene-isoprene-styrene, styrene-butadiene-styrene and styrene-ethylene-butylene-styrene. A family of such block copolymers are commercially available through Shell Chemical Company under the trade name "KRATON." Specific examples that are particularly useful for preparing unitary strands of this invention are KRATON 1107, KRATON 1111, KRATON 1101 and KRATON G 1657. Blends of these block copolymers may also be useful in forming unitary strands according to the invention.

Other components besides the thermoplastic elastomers may be utilized in unitary elastic strands. For example, many of the "KRATON" polymers can be made available as blends with mineral oil. Aromatic block reinforcing resins may, in some instances, be used to increase the size of the end block domains and increase the strength of the compositions. Light stabilizers, antioxidants and pigments may also be added. Generally each of the components of the compositions must be stable under extrusion conditions used to prepare the strands.

Typical conventional antioxidants usable include: thioethylene bis (3,5-di-tertiary-butyl-4-hydroxy)hydrocinnamate; tetrakis[methylene 3-(3',5'-ditertiary-butyl-4'-hydroxyphenyl)propionate]methane; 1.6-hexamethylene bis (3,5-ditertiary-butyl-4-hydroxy)hydrocinnamate; and, octadecyl(3,5-ditertiary-butyl-4-hydroxy)hydrocinnamate.

Typical conventional light stabilizers utilizable in compositions according to the present invention include phenolics such as 2-(2H-benzotriazol-2-yl)-p-cresol; octaphenyl salicylate; 2-(2'-hydroxy-3',5'-tertiaryamylphenyl)-benzotriazole; and, 2,4-dihydroxybenzophenone.

Other components which may be utilized in compositions according to the present invention include pigments, antiblock agents, fragrances, slip agents, fillers and dyes. Typically, such materials may be incorporated in amounts up to a total of about 20% of the weight of the strand, without substantially detrimentally affecting operation of the strand. In preferred applications of this invention, pigment is incorporated to impart desired color and opacity to the strand. A typical preferred pigment is titanium dioxide.

EXAMPLE 1

A mixture of the following components was made, heated to about 200° C., and was processed from a 30.0 millimeter (mm) extruder through a profiled die such as illustrated in FIG. 4, with the following dimensions: height of thicker regions (ribs) 0.38 mm; height of thinner regions of 0.15 mm; width of thicker regions (ribs) 1.27 mm; width of thinner regions (spacing between ribs) 1.65 mm. All percentages are by weight: 67.77% of a blend of 71% styrene-butadiene-styrene block copolymer and 29% plasticizing oil (KRATON 4141, Shell Chemical Co., Oakbrook, Ill.), 13.49% ethylene-vinyl acetate copolymer (Elvax 260 polymer, Dupont, Wilmington, Del.), 13.02% poly-alpha-methylstyrene (Amoco 18-290, Amoco Chemical Corp., Chicago, Ill.), 0.48% Tinuvin P ultraviolet light stabilizer (Ciba-Geigy Corporation, Cranston, R.I.), 0.48% Irganox 1010 antioxidant (Ciba-Geigy Corporation, Ardsley, N.Y.) and, 3.0% of a 50:50 mixture of polypropylene and titanium dioxide, CBE 101 P (C. B. Edwards, New Hope, Minn.). The cross-section of the resulting elastic strand had the same shape and approximately the same dimensions as the die orifice. The extrusion conditions were: screw speed 37 rpm, die pressure about 2300 psi (15850 kPa); and, line speed about 10.67 meters per minute.

EXAMPLE 2

Using the method and die of Example 1, and a similar die plate, the following copolymer was extruded to provide an elastic strand: an ethylene-vinyl acetate copolymer which was 46% by weight vinyl acetate (Elvax 46, Dupont, Wilmington, Del.). The profile of the die plate had the following dimensions: rib height 0.5 mm; rib width 1.61 mm; transition region thickness 0.15 mm; transition region width 2.16 mm. The extrusion conditions were: screw speed 37 rpm; die pressure about 816 psi; (5620 kPa); melt temperature 107° C.; and, line speed about 4 meters per minute. The cross-section of the resulting elastic strand had the same shape and profile and approximately the same dimensions as the die orifice.

EXAMPLE 3

Using the method of Example 1, and a die plate similar to that of Example 1, the following formulation was extruded to provide an elastic strand:

65.00% of a blend of 71% by weight styrene-butadiene-styrene block copolymer and 29% plasticizing oil (KRATON 4141, Shell Chemical Co., Oakbrook, Ill.), 13.00% ethylene-vinyl acetate copolymer (Elvax 260, Dupont, Wilmington, Del.), 5% antiblock agent CBE 13782E (C. B. Edwards, New Hope, Minn.), 1% erucamide slip concentrate, Ampacet 10110 (Ampacet Corp., Mt. Vernon, N.Y.), 12.50% Amoco 18-290, 2% CBE 101 P (a 50:50 mixture of polypropylene and titanium dioxide), 0.75% Irganox 1010 antioxidant and 0.75% Tinuvin P antioxidant. The profile of the die plate had the following dimensions: rib height 0.229 mm; rib width 1.270 mm; transition region thickness 0.18 mm; transition region width 1.6 mm. The extrusion conditions were: screw speed 41 rpm, die pressure about 3850 ps; (26500 kPa), melt temperature about 190° C.; and, line speed 10.67 meters/min. The cross-section of the resulting elastic strand had the same shape and profile, and approximately the same dimensions, as the die orifice, except that the width of the transition regions had a lower caliper than the orifice.

EXAMPLE 4

Using a sample of the elastic strand from Example 3, an unstretched and 200% stretched sample were set on a sheet of 38 micrometer polyethylene film and were heat sealed thereto using a "Sentinel" brand sealer Model 808 (Packaging Industries Group, Hyannis, Mass.). Attachment was constructed under pressure of about 290 kPa, a temperature of about 130° C. and a dwell time of five seconds. Each of the samples appeared sealed securely to the polyethylene film.

EXAMPLE 5

A 7.62 cm sample of the elastic strand of Example 3 was elongated 200% (to about 23 cm) and placed in a 65° C. oven for two minutes. The sample was allowed to cool, and the tension was released. A 15 cm test area was marked and the elastic was placed at 65° C. for five minutes under no tension. After cooling, the 15cm test area had shrunk to about 8.4 cm (45%).

EXAMPLE 6

A mixture of the following components was made and processed by extruding through a slot extrusion die into a nip where one roller was embossed with parallel grooves around the entire circumference, similarly to FIG. 11. The embossed pattern consisted of rectangular grooves with a width of 1.14 mm and a depth of 0.2 mm. The grooves were spaced 1.5 mm apart.

The mixture consisted of: 65.5% of a blend of 71% by weight styrene-butadiene-styrene block copolymer and 29% plasticizing oil (KRATON 4141, Shell Chemical Co., Oakbrook, Ill.), 13.00% ethylene-vinylacetate copolymer (Elvax 260, DuPont, Wilmington, Del.), 12.50% poly-alpha-methyl-styrene (Amoco 18-290, Amoco Chemical Corp., Chicago, Ill.), 5.00% antiblock agent (CBE 13782 E, C. B. Edwards, New Hope, Minn.), 1.00% UV stabilizer (Tinuvin P, Ciba-Geigy Corp., Cranston, R.I.), 1.00% antioxidant (Irganox 1010, Ciba-Geigy Corp., Ardsley, N.Y.), and 2.0% of a 50:50 mixture of titanium dioxide and polypropylene (CBE 101 P, C. B. Edwards, New Hope, Minn.).

The extrusion conditions were: screw speed 31 rpm; melt temperature about 200° C.; and, line speed about 10 m/min. The cross-section of the resulting elastic film had the same shape and profile as the embossed chill roller.

EXAMPLE 7

Using the method and embossed chill roller of Example 6, a profiled elastic film was made from Santoprene 201-87 thermoplastic rubber (Monsanto Chemical Co., Akron, Ohio).

The extrusion conditions were: screw speed 42 rpm; melt temperature 220° C.; and, line speed about 5 m/min. The cross-section of the resulting elastic film had the same shape and profile as the embossed chill roller.

It is to be understood that while certain embodiments of the present invention have been illustrated and described, the invention is not to be limited to the specific forms or arrangements herein described and shown.

What is claimed and desired to be secured by letters patent is as follows:

1. A garment; said garment comprising:
   (a) a shirred substrate; and
   (b) an elastic strand mounted on said substrate in a stretched state; said elastic strand composed of elastomeric material and having: a plurality of laterally spaced longitudinal ribs, each of said ribs having an overall first thickness of from 0.1 mm to 0.635 mm and an overall width of between about 0.25 mm and about 5.1 mm; and a substantially continuous longitudinal transition zone extending between and attached to each of said longitudinal ribs, each transition zone having a second thickness less than said first thickness, such that the ratio of said first thickness to said second thickness is from about 2/1 to 10/1 and each transition zone has an overall width of between about 0.25 mm and about 5.1 mm, the elastomeric material selected to provide the elastic strand with elasticity suitable to safely stretch around an arm, leg, or neck to provide a closing or sealing relationship wherein the substrate is shirred by shrinkage of the stretched elastic strand to which it is adhered.

2. A garment according to claim 1 wherein:
(a) said elastic strand has opposite first and second faces; and
(b) said second face is substantially flat and said ribs extend along said first face.

3. A garment according to claim 1 wherein:
(a) the sum of said overall width of each of said ribs divided by the number of ribs is an average width of said ribs; and
(b) an average transition zone width is at least 50% said average width of said ribs.

4. A garment according to claim 1 wherein said longitudinal ribs extend substantially parallel to one another.

* * * * *